(12) United States Patent
Katerberg et al.

(10) Patent No.: US 9,597,189 B2
(45) Date of Patent: Mar. 21, 2017

(54) PROSTHETIC TIBIAL COMPONENT FOR KNEE JOINT PROSTHESIS

(71) Applicant: Consensus Orthopedics, Inc., El Dorado Hills, CA (US)

(72) Inventors: Brian James Katerberg, Folsom, CA (US); Curt Wiedenhoefer, Davis, CA (US); Justin Anthony Creel, Fair Oaks, CA (US); James Anton Santangelo, Cool, CA (US)

(73) Assignee: Consensus Orthopedics, Inc., El Dorado Hills, CA (US)

( * ) Notice: Subject to any disclaimer, the term of this patent is extended or adjusted under 35 U.S.C. 154(b) by 0 days.

(21) Appl. No.: 13/871,993

(22) Filed: Apr. 26, 2013

(65) Prior Publication Data

US 2013/0289731 A1     Oct. 31, 2013

Related U.S. Application Data

(60) Provisional application No. 61/638,956, filed on Apr. 26, 2012.

(51) Int. Cl.
*A61F 2/38* (2006.01)
*A61F 2/46* (2006.01)
*A61F 2/30* (2006.01)

(52) U.S. Cl.
CPC ............ *A61F 2/389* (2013.01); *A61F 2/4684* (2013.01); *A61F 2002/3054* (2013.01); *A61F 2002/30332* (2013.01); *A61F 2002/30387* (2013.01); *A61F 2002/30484* (2013.01); *A61F 2002/30878* (2013.01); *A61F 2002/3895* (2013.01)

(58) Field of Classification Search
CPC ................... A61F 2/3868; A61F 2/389; A61F 2002/30484
USPC ........................................... 623/20.32–20.34
See application file for complete search history.

(56) References Cited

U.S. PATENT DOCUMENTS

| | | | |
|---|---|---|---|
| 5,358,530 A | | 10/1994 | Hodorek |
| 5,489,311 A | * | 2/1996 | Cipolletti ................... 623/20.34 |
| 5,702,466 A | * | 12/1997 | Pappas et al. ............. 623/20.29 |
| 6,080,195 A | * | 6/2000 | Colleran et al. ........... 623/20.32 |
| 6,709,461 B2 | * | 3/2004 | O'Neil et al. ............. 623/20.33 |
| 7,537,408 B2 | * | 5/2009 | Despres et al. ............... 403/279 |

OTHER PUBLICATIONS

Chun-Hsiung Huang et al., Fixed or Mobile-Bearing Total Knee Arthroplasty, Journal of Orthopaedic Surgery and Research, Jan. 5, 2007, 2:1.

* cited by examiner

*Primary Examiner* — Brian Dukert
(74) *Attorney, Agent, or Firm* — Pandiscio & Pandiscio

(57) ABSTRACT

A prosthetic tibial component for a knee joint, said prosthetic tibial component comprising:
  a base construct for engaging the tibia; and
  a bearing construct for engaging the femoral side of the knee joint;
  said bearing construct being adjustably fixedly mountable to said base construct.

14 Claims, 13 Drawing Sheets

PROSTHETIC TIBIAL COMPONENT FOR KNEE JOINT PROSTHESIS

REFERENCE TO PENDING PRIOR PATENT APPLICATION

This patent application claims benefit of pending prior U.S. Provisional Patent Application Ser. No. 61/638,956, filed Apr. 26, 2012 by Brian James Katerberg et al. for MODULAR TRAY, which patent application is hereby incorporated herein by reference.

FIELD OF THE INVENTION

This invention relates to orthopedic prostheses in general, and more particularly to prosthetic tibial components for knee joint prostheses.

BACKGROUND OF THE INVENTION

Joint replacement surgery seeks to replace some or all of a natural joint with prosthetic components so as to provide long-lasting function and pain-free mobility.

For example, in the case of a prosthetic total hip joint, the head of the femur is replaced with a prosthetic femoral stem component, and the socket of the acetabulum is replaced by a prosthetic acetabular cup component, whereby to provide a prosthetic total hip joint.

In the case of a prosthetic total knee joint, the top of the tibia is replaced by a prosthetic tibial component, and the bottom of the femur is replaced by a prosthetic femoral component, whereby to provide a prosthetic total knee joint.

The present invention is directed to orthopedic prostheses for restoring the knee joint and, in particular, to improved prosthetic tibial components.

Looking now at FIG. 1, there is shown a prior art prosthetic total knee joint 5 which generally comprises a prosthetic tibial component 10 secured to the top end of a resected tibia 15, and a prosthetic femoral component 20 which is secured to the bottom end of a resected femur 25.

A typical prior art prosthetic tibial component 10 is shown in greater detail in FIGS. 2 and 3. Prior art prosthetic tibial component 10 generally comprises a metal base construct 30 and a polyethylene bearing construct 35.

More particularly, metal base construct 30 generally comprises a baseplate 40 having a top surface 42 and a bottom surface 43, a stem 45 and a plurality of posts 50 descending from bottom surface 43 of baseplate 40 and into resected tibia 15, and a plurality of screws 55 passing through baseplate 40 and into resected tibia 15. Baseplate 40 preferably has a peripheral profile which generally matches the peripheral profile of the resected tibia 15. Metal base construct 30 also comprises a pair of locking rails 60 fixed to the top surface 42 of baseplate 40 and defining a groove 65 therebetween, and a pair of end walls 70 connected to top surface 42 of baseplate 40. Preferably bottom surface 43 of baseplate 40 (and, optionally, stem 45 and/or posts 50) comprises a porous material so as to allow bone ingrowth into baseplate 40 (and/or stem 45 and/or posts 50), whereby to facilitate osseo-integration of baseplate 40 (and/or stem 45 and/or posts 50) with resected tibia 15 over time. Additionally and/or alternatively, baseplate 40 and/or stem 45 and/or posts 50 may be fixed to resected tibia 15 with bone cement.

Polyethylene bearing construct 35 comprises a sculpted upper surface 71 having a central ridge 72 which separates a pair of scalloped seats 73 for receiving the condyles (either natural or prosthetic) of the lower femur. Polyethylene bearing construct 35 also comprises a flat bottom surface 75 having a recess 80 in which is disposed a tongue 85. Tongue 85 is sized to slidingly fit in the groove 65 which is defined by locking rails 60 of metal base construct 30 (FIG. 3), whereby polyethylene bearing construct 35 may be slidingly secured to locking rails 60 of metal base construct 30. Note that end walls 70 of locking metal base construct 30 act as stops for polyethylene bearing construct 35 when tongue 85 of polyethylene bearing construct 35 is advanced into the groove 65 which is defined by locking rails 60 of metal base construct 30.

In use, the top end of tibia 15 is resected, and metal base construct 30 is secured to tibia 15, i.e., by advancing stem 45 and posts 50 into resected tibia 15 until bottom surface 43 of baseplate 40 is seated against resected tibia 15. Note that the parallel dispositions of stem 45 and posts 50 facilitates advancement of stem 45 and posts 50 into the resected tibia. Next, screws 55 are advanced through baseplate 40 and into resected tibia 15, whereby to secure metal base construct 30 to resected tibia 15. Then polyethylene bearing construct 35 is locked onto metal base construct 30, e.g., by sliding tongue 85 of polyethylene bearing construct 35 into the groove 65 which is defined by locking rails 60 of metal base construct 30 until polyethylene bearing construct 35 engages end walls 70 of baseplate 40. Thereafter, the knee joint is reduced, allowing the condyles (either natural or prosthetic) of the lower femur to settle into the scalloped seats 73 of polyethylene bearing construct 35.

Unfortunately, in some patients, the natural geometry of the knee is such that there may be some degree of misalignment between the condyles (either natural or prosthetic) of the lower femur and the scalloped seats 73 of polyethylene bearing construct 35 of the prosthetic tibial component 10. Specifically, the anterior-posterior centerline of the condyles (either natural or prosthetic) of the lower femur, and the anterior-posterior centerline of the scalloped seats 73 of polyethylene bearing construct 35 of the prosthetic tibial component 10, may be angularly offset from one another. As a result, the condyles (either natural or prosthetic) of the lower femur may not seat properly in the scalloped seats 73 of polyethylene bearing construct 35 of the prosthetic tibial component 10. This may occur at some or all of the extent of flexure of the knee. This mis-seating of the condyles (either natural or prosthetic) of the lower femur in the scalloped seats 73 of polyethylene bearing construct 35 of the prosthetic tibial component 10 can lead to reduced stability of the knee in both static and dynamic conditions, and can lead to excessive wear of the polyethylene bearing construct 35 over time. In addition, this mis-seating of the condyles (either natural or prosthetic) of the lower femur in the scalloped seats 73 of polyethylene bearing construct 35 of the prosthetic tibial component 10 can lead to early loosening of the prosthetic tibial component, or to early loosening of the prosthetic femoral component, or both, and/or it can result in poor bone coverage leading to bone subsidence.

Thus there is a need for a new and improved prosthetic tibial component for a knee joint prosthesis which can provide for better alignment between the condyles (either natural or prosthetic) of the lower femur and the scalloped seats of the polyethylene bearing construct of the prosthetic tibial component.

SUMMARY OF THE INVENTION

The present invention comprises the provision and use of a new and improved prosthetic tibial component for a knee joint prosthesis which provides for better alignment between the condyles (either natural or prosthetic) of the lower femur and the scalloped seats of the polyethylene bearing construct of the prosthetic tibial component.

More particularly, the present invention comprises the provision and use of a new and improved prosthetic tibial component for a knee joint prosthesis which provides for better alignment of the anterior-posterior centerline of the condyles (either natural or prosthetic) of the lower femur and the anterior-posterior centerline of the scalloped seats of the polyethylene bearing construct of the prosthetic tibial component.

In one preferred form of the invention, there is provided a prosthetic tibial component for a knee joint, said prosthetic tibial component comprising:

a base construct for engaging the tibia; and
a bearing construct for engaging the femoral side of the knee joint;
said bearing construct being adjustably fixedly mountable to said base construct.

In another preferred form of the invention, there is provided a method for reconstructing a knee joint, said method comprising:

providing a prosthetic tibial component for a knee joint, said prosthetic tibial component comprising a base construct for engaging the tibia, and a bearing construct for engaging the femoral side of the knee joint, said bearing construct comprising a pair of concave seats for receiving the condyles of the femoral side of the knee joint, and said bearing construct being adjustably fixedly mountable to said base construct;

resecting the tibia; and
mounting said base construct to said resected tibia and adjustably fixedly mounting said bearing construct to said base construct so that said pair of concave seats in said bearing construct are appropriately aligned with the condyles of the femoral side of the knee joint.

In another preferred form of the invention, there is provided a prosthetic tibial component for a knee joint, said prosthetic tibial component comprising:

a base construct comprising a baseplate for attachment to the tibia and a mount for receiving a bearing construct for engaging the femoral side of the knee joint, said mount being adjustably fixedly mountable to said baseplate.

In another preferred form of the invention, there is provided a prosthetic component for a joint, said prosthetic component comprising:

a base construct for engaging a first bone of the joint; and
a bearing construct for engaging a second bone of the joint;
said bearing construct being adjustably fixedly mountable to said base construct.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Novel Prosthetic Tibial Component

The present invention comprises the provision and use of a new and improved prosthetic tibial component for a knee joint prosthesis which provides for better alignment between the condyles (either natural or prosthetic) of the lower femur and the scalloped seats of the polyethylene bearing construct of the prosthetic tibial component.

More particularly, the present invention comprises the provision and use of a new and improved prosthetic tibial component for a knee joint prosthesis which provides for better alignment of the anterior-posterior centerline of the condyles (either natural or prosthetic) of the lower femur and the anterior-posterior centerline of the scalloped seats of the polyethylene bearing construct of the prosthetic tibial component.

Figure 1:
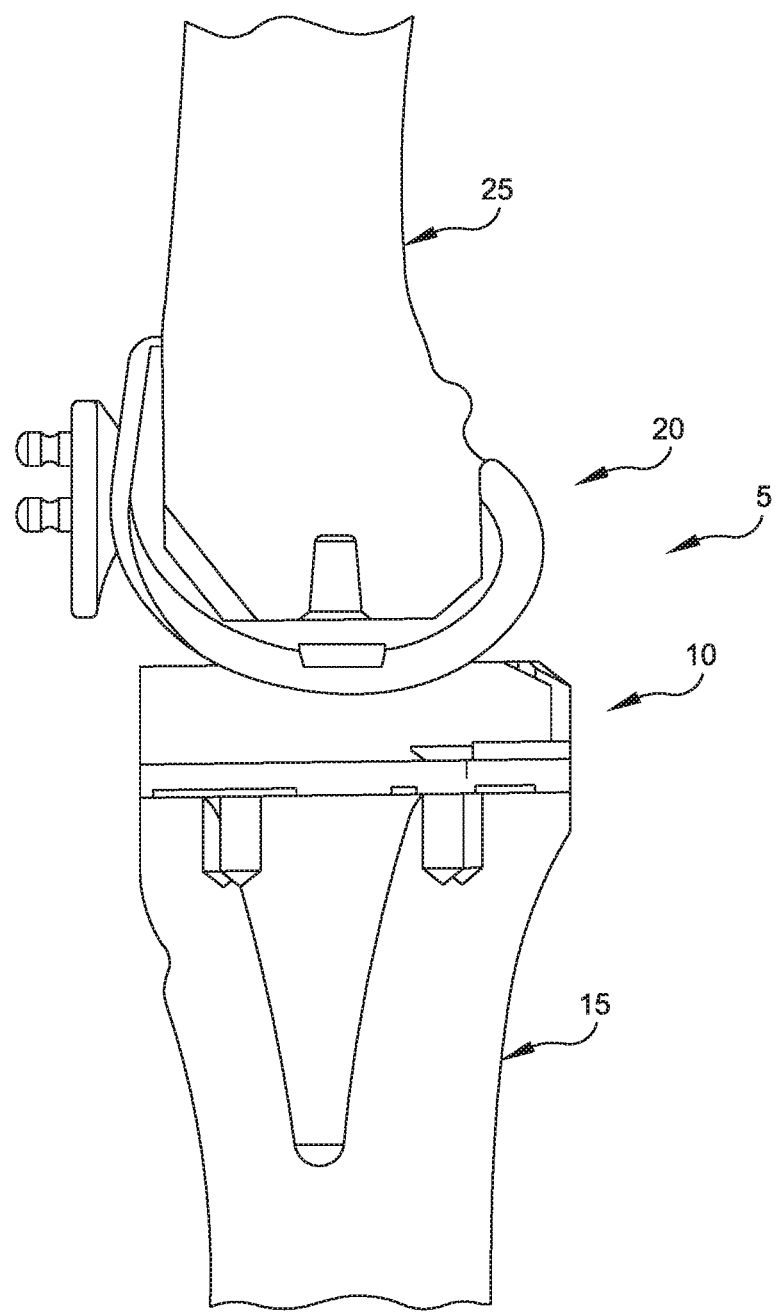
FIG. 1 is a schematic side view showing a prior art prosthetic total knee joint.
Figure 2:
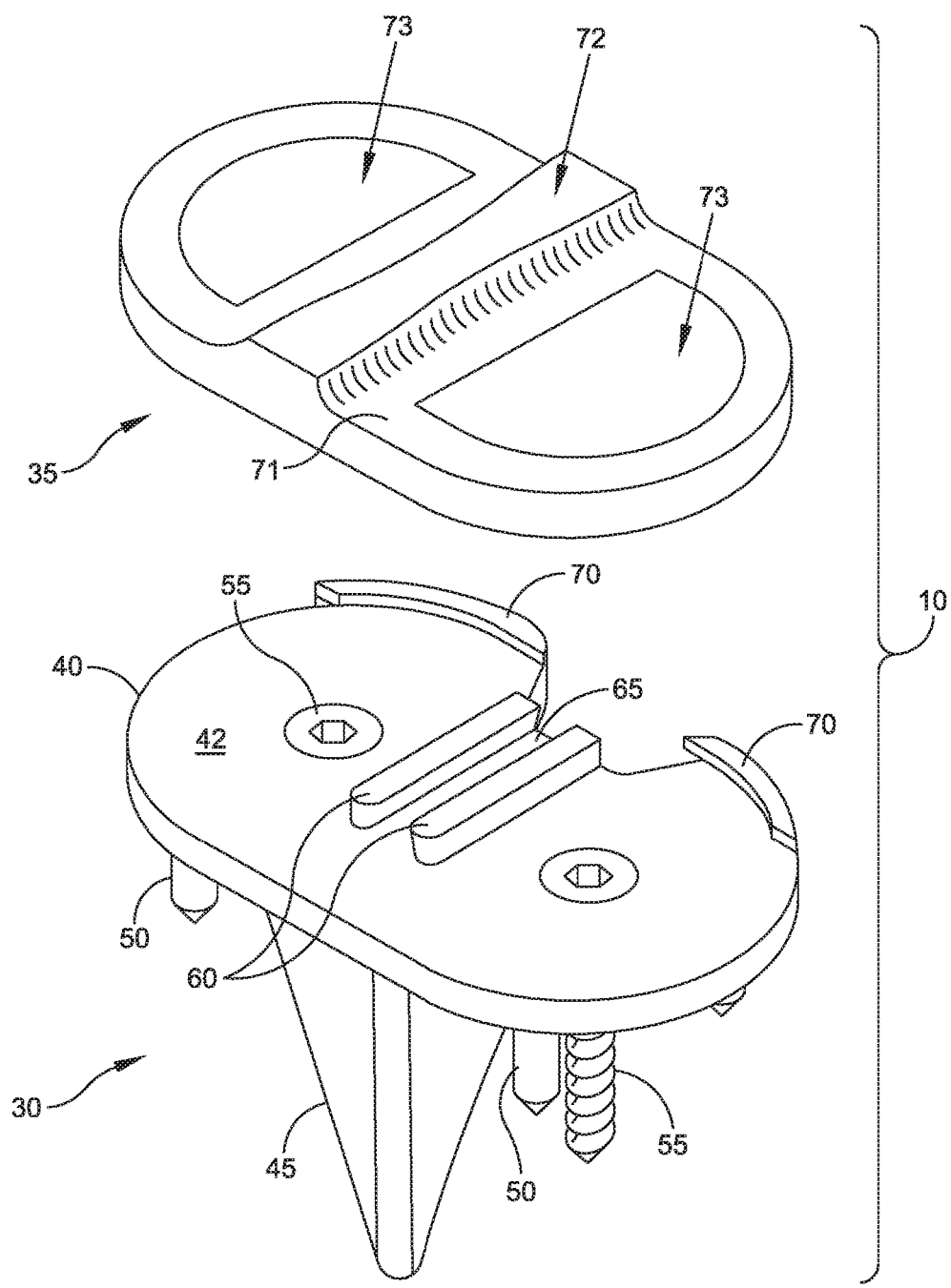
FIG. 2 is a schematic partially-exploded perspective view showing a prior art prosthetic tibial component.
Figure 3:
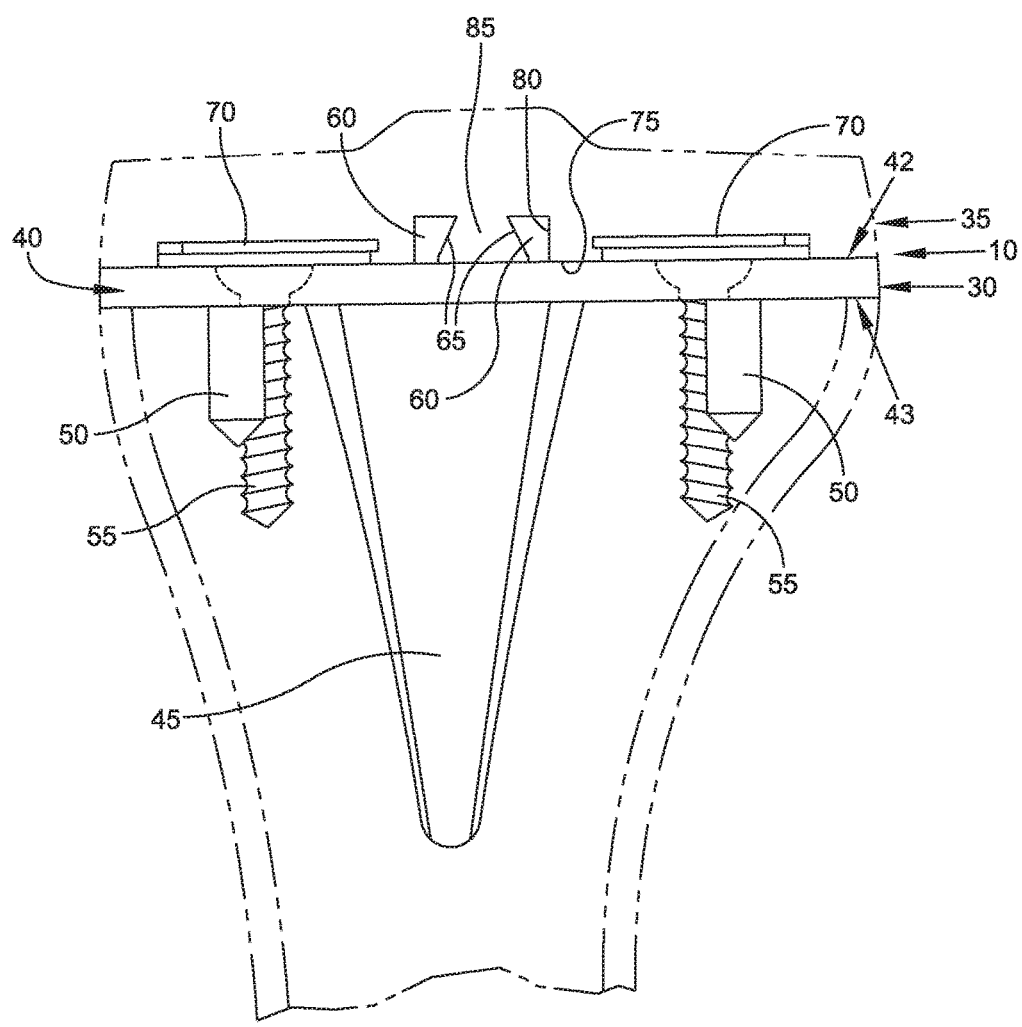
FIG. 3 is a schematic front view showing a prior art prosthetic tibial component secured to a resected tibia.
Figure 4:
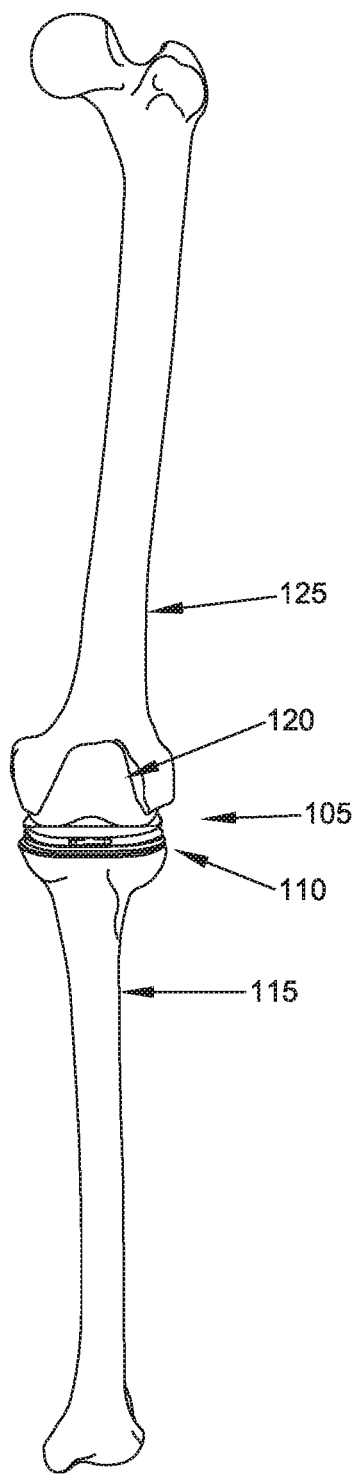
FIG. 4 is a schematic view showing a reconstructed knee joint, wherein the tibial side of the reconstructed knee joint comprises a novel prosthetic tibial component which is secured to the top end of a resected tibia, and the femoral side of the reconstructed knee joint comprises a prosthetic femoral component which is secured to the bottom end of a resected femur.

Looking now at FIG. 4, there is shown a novel prosthetic total knee joint 105 which generally comprises a novel prosthetic tibial component 110 secured to the top end of a resected tibia 115, and a prosthetic femoral component 120 which is secured to the bottom end of a resected femur 125.

Figure 5:
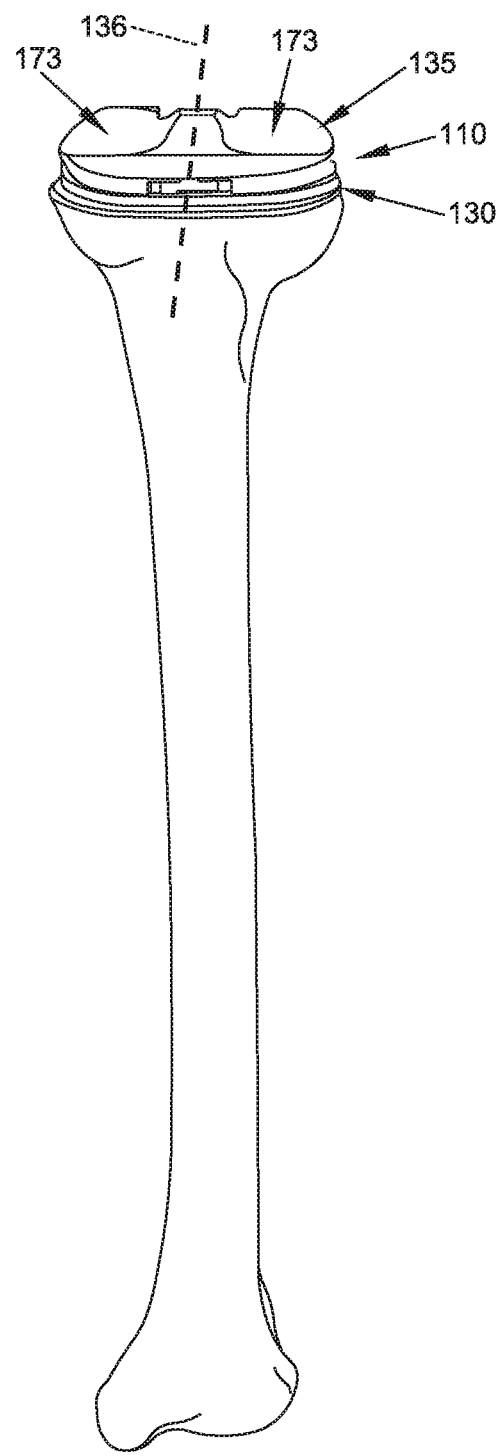
FIG. 5 is a schematic view showing the tibial side of the reconstructed knee joint shown in FIG. 4.

As will hereinafter be discussed in further detail, and looking now at FIG. 5, novel prosthetic tibial component 110 generally comprises a modular metal base construct 130 and a polyethylene bearing construct 135. As will also hereinafter be discussed in further detail, novel prosthetic tibial component 110 is characterized by two scalloped seats 173 which define an anterior-posterior centerline 136 of the polyethylene bearing construct 135.

Figure 6:
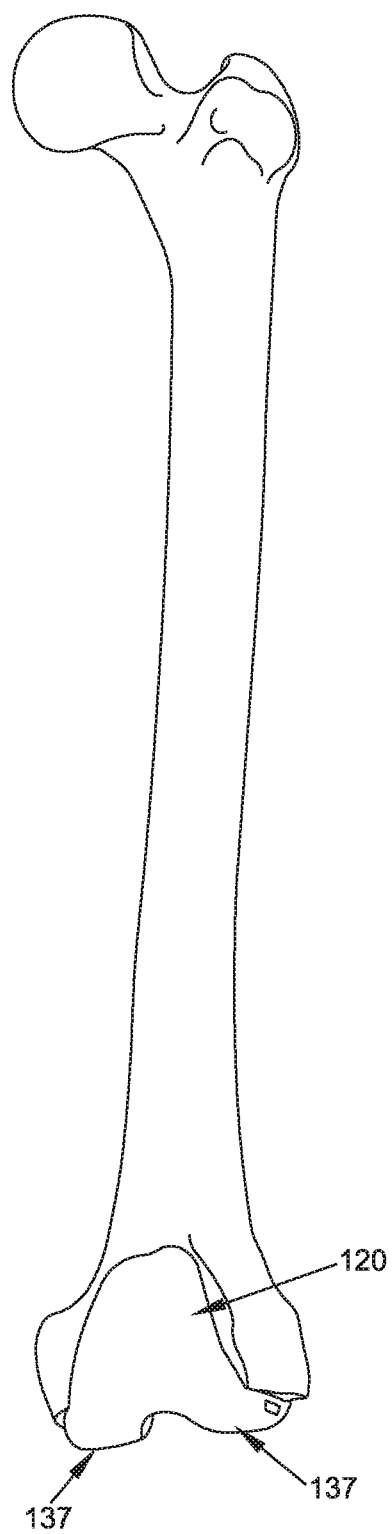
FIGS. 6 and 7 are schematic views showing the femoral side of the reconstructed knee joint shown in FIG. 4.
Figure 7:
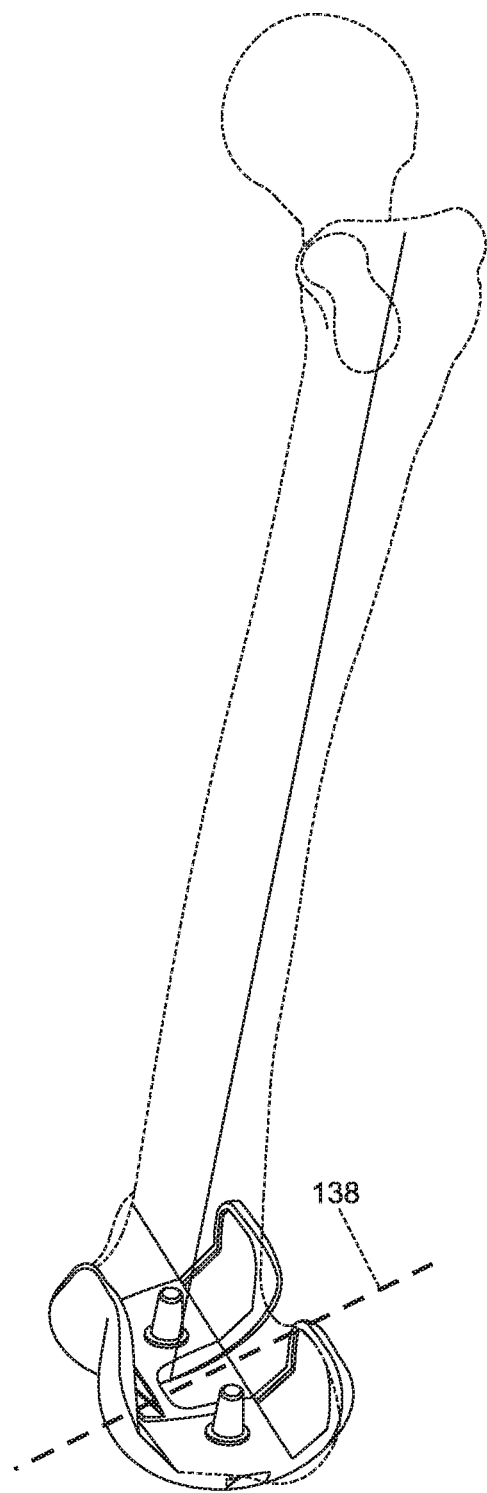

Prosthetic femoral component 120 is shown in greater detail in FIGS. 6 and 7, and is characterized by two condyles 137 which define an anterior-posterior centerline 138.

As will hereinafter be discussed, novel prosthetic tibial component 110 is configured so as to allow the anterior-posterior centerline 136 of the scalloped seats of polyethylene bearing construct 135 to be better aligned with the anterior-posterior centerline 138 of the two condyles 137 of the lower femur, whereby to provide for better alignment between the condyles of the lower femur and the scalloped seats of the polyethylene bearing construct.

Figure 8:
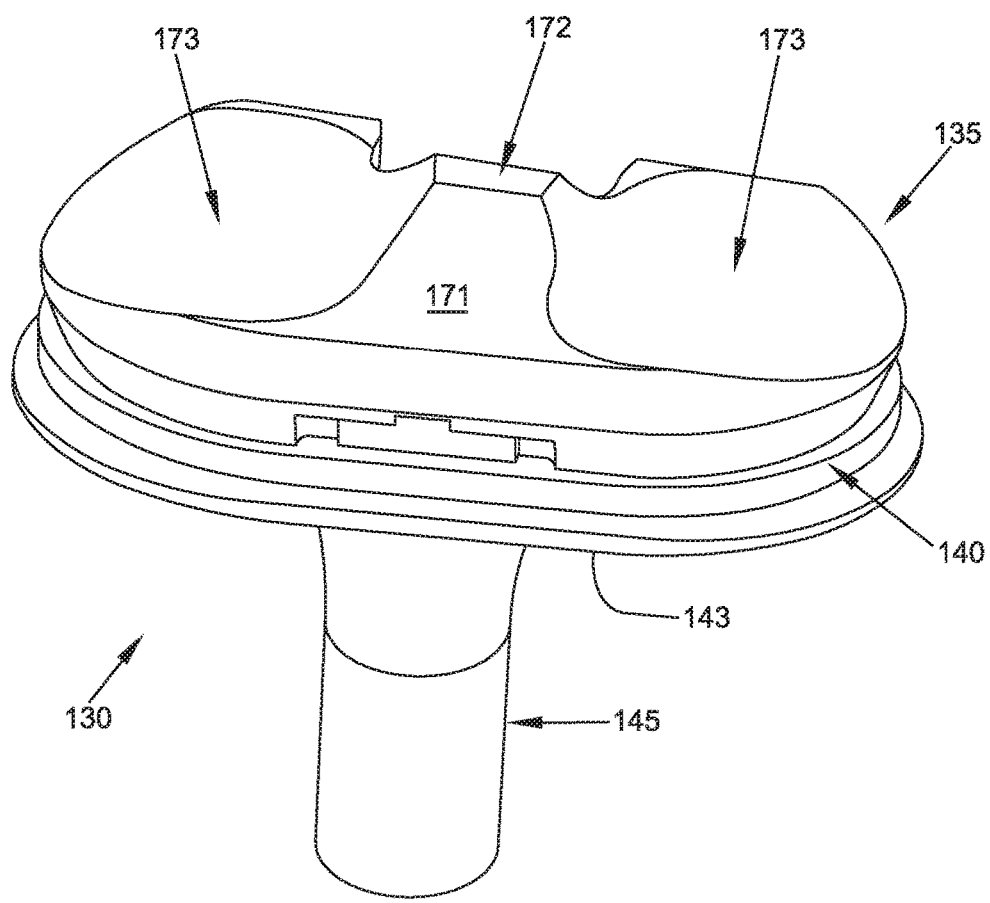
FIGS. 8 and 9 are schematic views showing the novel prosthetic tibial component shown in FIG. 4.
Figure 9:
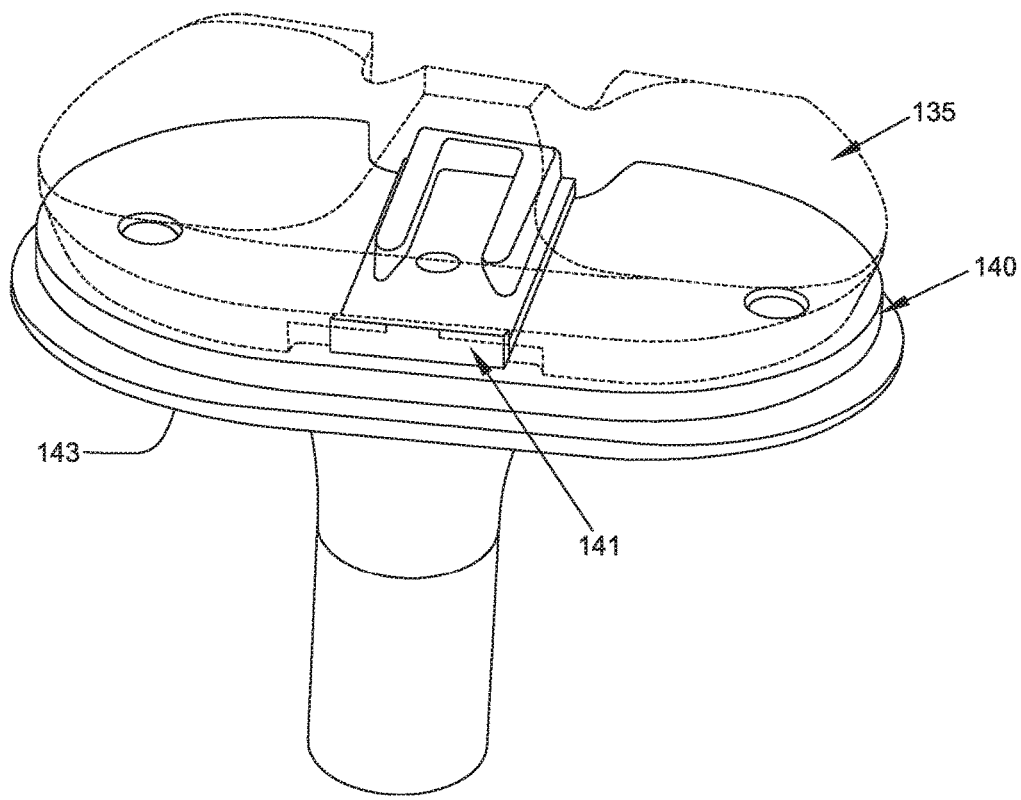
Figure 10:
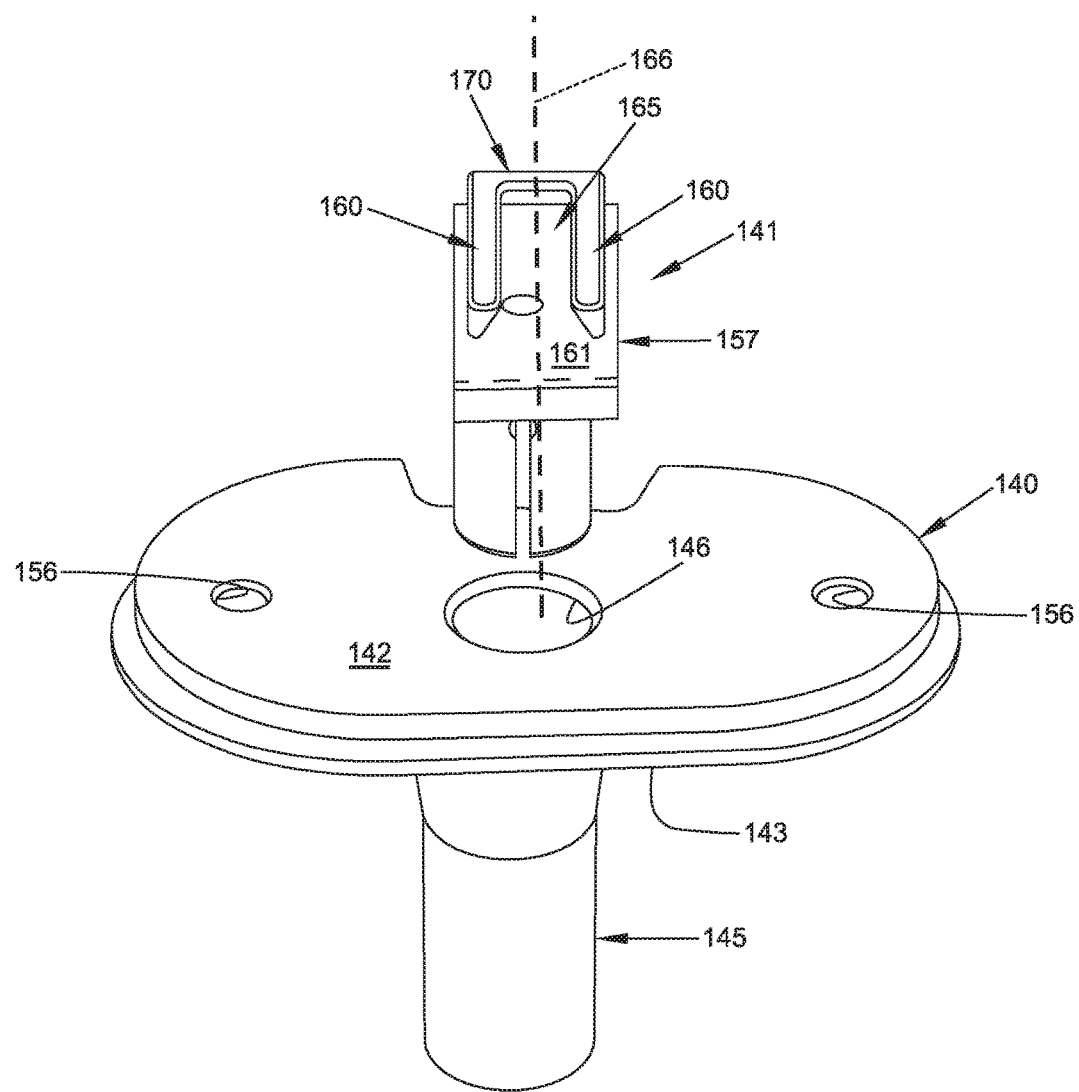
FIG. 10 is a schematic exploded view showing the modular metal base construct of the novel prosthetic tibial component shown in FIGS. 8 and 9.

More particularly, and looking now at FIGS. 8-10, modular metal base construct 130 generally comprises a baseplate 140 and a locking rail component 141.

Baseplate 140 has a top surface 142 for receiving polyethylene bearing construct 135, an opposing bottom surface 143 for engaging resected tibia 115, a stem 145 descending from the bottom surface of baseplate 140 for extending into resected tibia 115, a bore 146 extending through baseplate 140 and into stem 145, and a plurality of screw holes 156 extending through baseplate 140 for receiving screws (not shown) for securing baseplate 140 to resected tibia 115. Baseplate 140 preferably has a peripheral profile which generally matches the peripheral profile of the resected tibia 115.

Locking rail component 141 comprises a body 157 having a pair of locking rails 160 running along its top surface 161 and defining a groove 165 therebetween. Groove 165 extends along a longitudinal axis 166. Body 157 of locking rail component 141 also has an end wall 170 connected to top surface 161 of body 157 and connecting locking rails 160 to one another. A post 169 descends from body 157 of locking rail component 141 and is sized to be received in bore 146 of baseplate 140 and secured therein. Preferably the bottom surface 143 of baseplate 140 (and, optionally, stem 145) comprises a porous material so as to allow bone ingrowth into baseplate 140 (and/or stem 145), whereby to facilitate osseo-integration of the baseplate 140 (and/or stem 145) with resected tibia 115 over time. Additionally and/or alternatively, baseplate 140 and/or stem 145 may be fixed to resected tibia 115 with bone cement.

Figure 11:
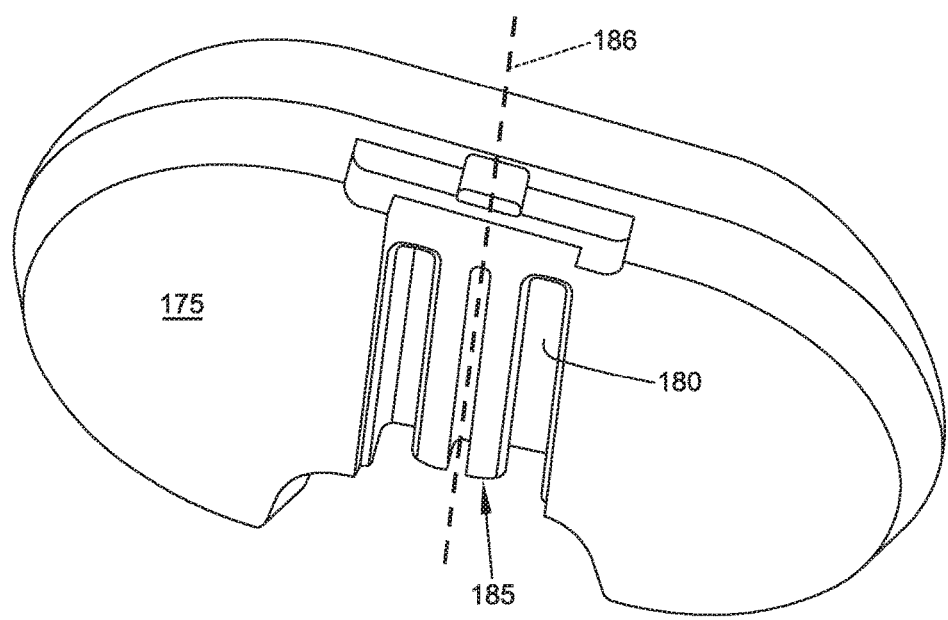
FIG. 11 is a schematic view showing the polyethylene bearing construct of the novel prosthetic tibial component shown in FIGS. 8 and 9.

Looking now at FIGS. 8, 9 and 11, polyethylene bearing construct 135 comprises a sculpted upper surface 171 having a central ridge 172 which separates a pair of scalloped seats 173 for receiving the condyles (either natural or prosthetic) of the lower femur. Polyethylene bearing construct 135 also comprises a flat bottom surface 175 having a recess 180 in which is disposed a tongue 185 which extends along a longitudinal axis 186. Note that longitudinal axis 186 of tongue 185 extends parallel to the anterior-posterior centerline 136 of scalloped seats 173 of the polyethylene bearing construct 135. Tongue 185 is sized to slidingly fit in groove 165 of locking rails 160 of locking rail component 141 (FIG. 11), whereby polyethylene bearing construct 135 may be slidingly secured to locking rail component 141 of modular metal base construct 130. Note that end wall 170 of locking rail component 141 acts as a stop for polyethylene bearing construct 135 when tongue 185 of polyethylene bearing construct 135 is advanced into groove 165 of locking rail component 141 of modular metal base construct 130. Note also that when polyethylene bearing construct 135 is mounted to locking rail component 141, the anterior-posterior centerline 136 of the scalloped seats 173 of the polyethylene bearing construct 135, and the longitudinal axis 186 of the tongue 185 of polyethylene bearing construct 135, both extend parallel to longitudinal axis 166 of groove 165 of locking rail component 141.

Use of the Novel Prosthetic Tibial Component

In use, the top end of tibia 115 is first resected.

Next, baseplate 140 is secured to tibia 115, i.e., by advancing stem 145 into resected tibia 115 until the bottom surface 143 of baseplate 140 is seated against resected tibia 115, and by advancing screws through holes 156 of baseplate 140 and into resected tibia 115, whereby to secure baseplate 140 to resected tibia 115.

Figure 12A:
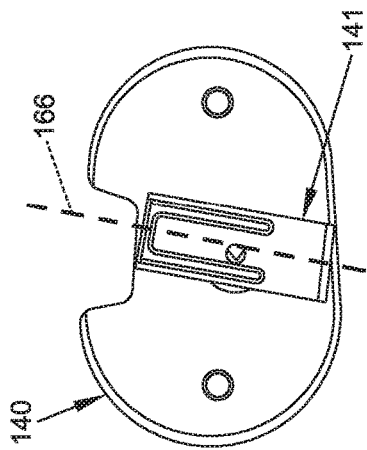
FIGS. 12A, 12B and 12C show the locking rail element of the modular metal base construct of FIG. 10 in a range of angular positions (i.e., FIG. 12A shows the locking rail element externally rotated, FIG. 12B shows the locking rail element in a "neutral" position, and FIG. 12C shows the locking rail element internally rotated)
Figure 12B:
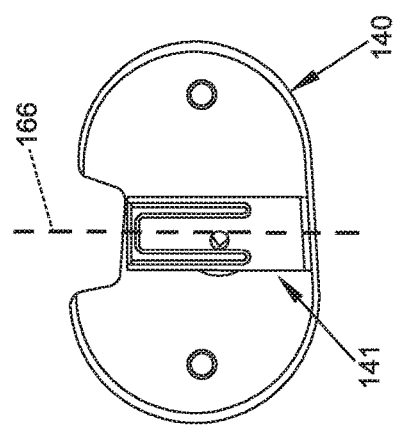
Figure 12C:
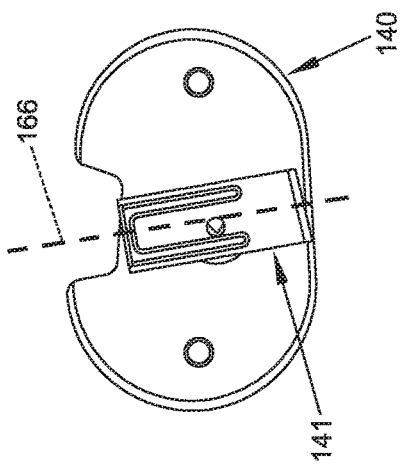

Then locking rail component 141 is mounted to baseplate 140 by advancing post 169 of locking rail component 141 into bore 146 of baseplate 140 and fixedly locking post 169 in bore 146, whereby to fixedly secure locking rail component 141 vis-à-vis baseplate 140. Note that prior to fixedly securing locking rail component 141 to baseplate 140, the angular disposition of locking rail component 141 is carefully adjusted vis-à-vis baseplate 140 (and hence vis-à-vis resected tibia 115), such that the longitudinal axis 166 of groove 165 of locking rail component 141 is aligned with the anterior-posterior centerline 138 of the two condyles 137 of the lower femur (which will thereafter assure, when polyethylene bearing construct 135 is mounted to locking rail component 141, that the anterior-posterior centerline 136 of the scalloped seats 173 of polyethylene bearing construct 135 are appropriately aligned with the anterior-posterior centerline 138 of the two condyles 137 of the lower femur). By way of example but not limitation, as seen in FIGS. 12A, 12B and 12C, the longitudinal axis 166 of groove 165 of locking rail component 141 is oriented to an appropriate angular position relative to baseplate 140 so that the longitudinal axis 166 of groove 165 is appropriately aligned with the anterior-posterior centerline 138 of the two condyles 137 of the lower femur.

Figure 13A:
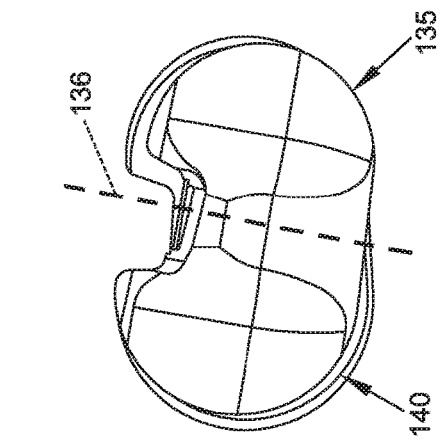
FIGS. 13A, 13B and 13C are views similar to those of FIGS. 12A, 12B and 12C, respectively, but with the polyethylene bearing construct shown mounted to the modular metal base construct (i.e., FIG. 13A shows the polyethylene bearing construct externally rotated, FIG. 13B shows the polyethylene bearing construct in a "neutral" position, and FIG. 13C shows the polyethylene bearing construct internally rotated)
Figure 13B:
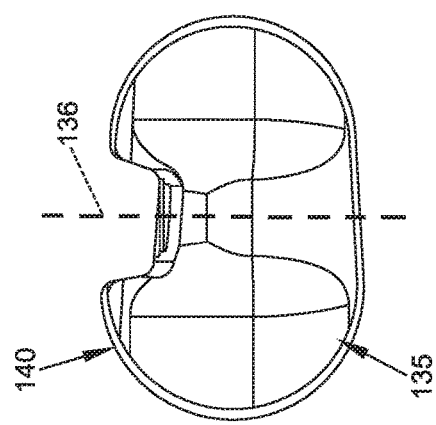
Figure 13C:
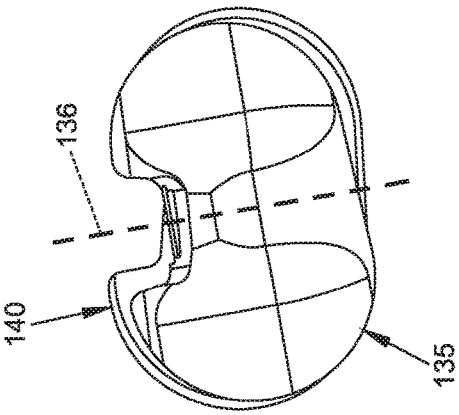

Next, polyethylene bearing construct 135 is locked onto modular metal base construct 130, e.g., by sliding tongue 185 of polyethylene bearing construct 135 into groove 165 of locking rail component 141 of modular metal base construct 130 until polyethylene bearing construct 135 engages end wall 170 of locking rail component 141. This action will cause the anterior-posterior centerline 136 of the scalloped seats 173 of polyethylene bearing construct 135 to be aligned with the longitudinal axis of groove 165 of locking rail component 141 (see FIGS. 13A, 13B and 13C), and hence appropriately aligned with the anterior-posterior centerline 138 of the two condyles 137 of the lower femur. Note that polyethylene bearing construct 135 may be offered in a range of sizes so as to minimize any "overhang" vis-à-vis baseplate 140 when polyethylene bearing construct 135 is set in an externally rotated position (FIG. 13A) or in an internally rotated position (FIG. 13C).

Thereafter, the joint is reduced, allowing the condyles (either natural or prosthetic) of the lower femur to settle into the scalloped seats 173 of polyethylene bearing construct 135 of prosthetic tibial component 110.

If, after the joint is reduced, it is found that the kinematics of the joint are not satisfactory, the joint can be distracted again, polyethylene bearing construct 135 can be removed, locking rail component 141 can be repositioned vis-à-vis baseplate 140, polyethylene bearing construct 135 can be remounted to locking rail component 141, and then the joint can be reduced again. In this way, optimal positioning of the anterior-posterior centerline 136 of the scalloped seats 173 of polyethylene bearing construct 135 can be achieved vis-à-vis the anterior-posterior centerline 138 of the two condyles 137 of the lower femur.

Furthermore, if revision surgery should subsequently be required to adjust the positioning of the anterior-posterior centerline 136 of the scalloped seats 173 of polyethylene bearing construct 135, this can be achieved in a similar manner.

Mounting the Locking Rail Component to the Baseplate

Figure 14:
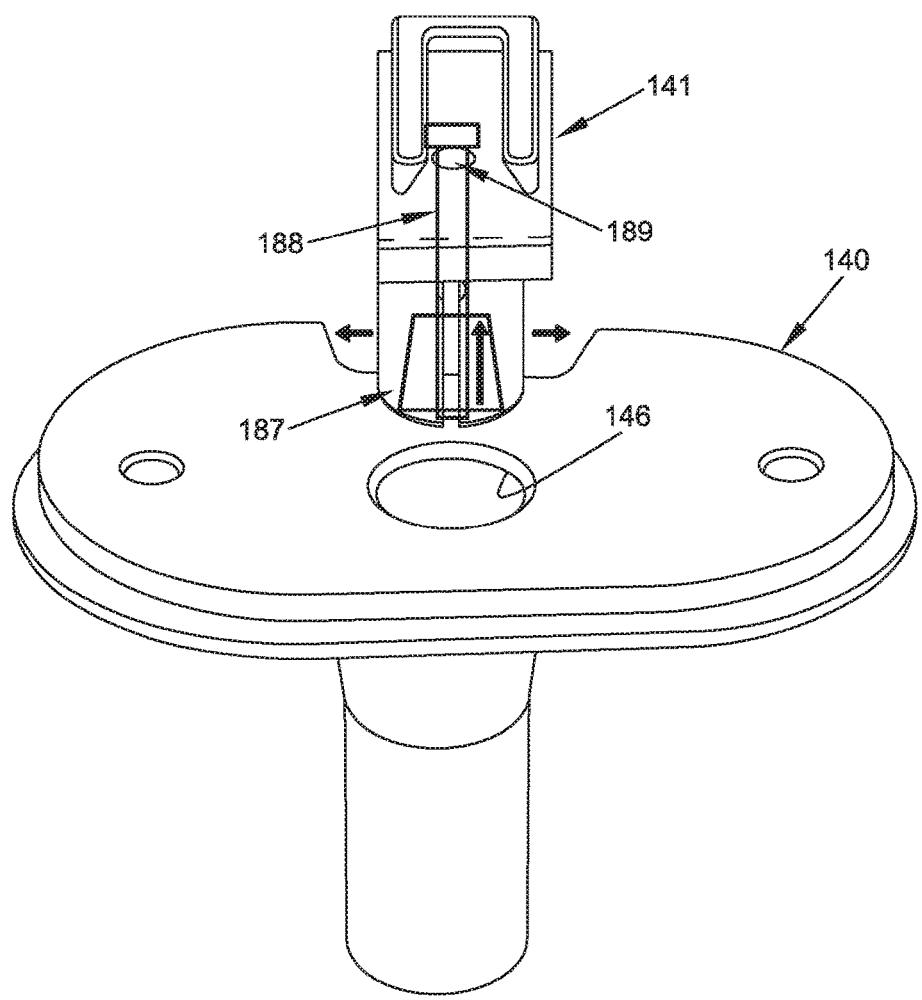
FIG. 14 is a schematic view showing one preferred construction for securing the locking rail element to the remainder of the modular metal base construct.

As discussed above, post 169 of locking rail component 141 is advanced into bore 146 of baseplate 140 and fixedly locked in position, whereby to fixedly secure locking rail component 141 to baseplate 140. It will be appreciated that various arrangements may be provided to effect this securement. By way of example but not limitation, and looking now at FIG. 14, post 169 may receive an expanding collet 187 so as to cause post 169 to radially expand and thereby "grip" the side wall of bore 146 of baseplate 140. More particularly, in this construction, a screw 188 may pass through a hole 189 formed in body 157 of locking rail component 141 so as to pull collet 187 proximally, whereby to radially expand post 169 within bore 146 and fixedly secure post 169 in bore 146.

Alternatively, and by way of further example, post 169 may comprise a Morse taper for binding with the side wall of bore 146 of baseplate 140.

Or, by way of still further example, post 169 may be formed with a compressible design for forming a friction grip with the side wall of bore 146.

And post 169 and recess 146 of baseplate 140 may be formed with threads for fixedly securing post 169 in recess 146.

In still another form of the invention, a male-female connection is used to fixedly secure locking rail component 141 to baseplate 140, but in this alternative form of the invention, the male portion of the connection is formed on baseplate 140 and the female portion of the connection is formed on locking rail component 141.

Still other approaches for securing locking rail component 141 to baseplate 140 will be apparent to those skilled in the art in view of the present disclosure.

Further Aspects of the Invention

In addition to the foregoing, it should also be appreciated that polyethylene bearing construct 135 may be mounted to locking rail component 141 before the locking rail component 141 is mounted to baseplate 140, and/or locking rail component 141 may be mounted to baseplate 140 before baseplate 140 is mounted to resected tibia 115.

Also, while in the foregoing description the novel prosthetic tibial component is discussed in the context of use with a prosthetic femoral component, it should be appreciated that the novel prosthetic tibial component may be used in conjunction with the natural condyles of a femur.

And it should be appreciated that the present invention is not restricted to "dual-compartment" knee joint reconstructions, i.e., it may also be applied to "uni-compartment" knee joint reconstructions where only one scalloped seat 173 and one femoral condyle is involved.

In addition to the foregoing, it should be appreciated that it is common in the orthopedic field to test a joint reconstruction using "trial" components prior to committing to the joint reconstruction using the actual prosthetic components. In this respect it should be appreciated that the present invention may be applied to trial components as well as to the actual prosthetic components.

Application to Other Joints

It should be appreciated that the present invention may be utilized in prostheses for joints other than the knee. By way of example but not limitation, the present invention may be utilized in an elbow joint prosthesis, an ankle joint prosthesis, a spinal prosthesis, etc.

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A prosthetic tibial component for a knee joint, said prosthetic tibial component comprising:
   a base construct for engaging the tibia, the base construct comprising a bore;
   a bearing construct for engaging the femoral side of the knee joint, the bearing construct comprising one of a horizontally-oriented tongue and groove; and
   a mount interposed between the base construct and the bearing construct for mounting the bearing construct to the base construct, the mount comprising (i) a post configured for positioning within the bore of the base construct and rotation to a user-selected angular orientation after the base construct has been disposed in a bone, and (ii) a locking mechanism for locking the post within the bore of the base construct with the user-selected angular orientation after the base construct has been disposed in a bone, so as to secure the mount to the base construct with the user-selected angular orientation, and the mount further comprising the other of the horizontally-oriented tongue and groove for slidably receiving the bearing construct and locking the bearing construct to the mount;
   wherein the horizontally-oriented groove comprises two vertically-extending walls, with each vertically-extending wall terminating in a horizontally-extending projection, and with the two vertically-extending walls being spaced from one another;
   wherein the horizontally-oriented tongue comprises a vertically-extending member terminating in a pair of laterally-extending projections;
   and further wherein the vertically-extending member of the tongue is sized to fit between the horizontally-extending projections of the groove and the pair of laterally-extending projections of the tongue are sized to fit between the pair of vertically-extending walls of the groove.

2. A prosthetic tibial component according to claim 1 wherein said bearing construct is translationally fixedly mountable to said base construct.

3. A prosthetic tibial component according to claim 2 wherein said bearing construct is angularly adjustably fixedly mountable to said base construct.

4. A prosthetic tibial component according to claim 3 wherein said base construct comprises a planar surface, and further wherein the axis of the angular adjustment of said bearing construct relative to said base construct is perpendicular to said planar surface of said base construct.

5. A prosthetic tibial component according to claim 1 wherein said base construct comprises a baseplate for attachment to the tibia, and further wherein said mount is adjustably fixedly mountable to said baseplate.

6. A prosthetic tibial component according to claim 5 wherein said mount is angularly adjustably fixedly mountable to said baseplate.

7. A prosthetic tibial component according to claim 6 wherein said baseplate comprises a planar surface, and further wherein the axis of the angular adjustment of said mount relative to said baseplate is perpendicular to said planar surface of said baseplate.

8. A prosthetic tibial component according to claim 1 wherein said post is configured to be locked within the bore of the base construct by a friction fit.

9. A prosthetic tibial component according to claim 8 wherein said friction fit is created by radial expansion of said post.

10. A prosthetic tibial component according to claim 9 wherein radial expansion of said post is created by longitudinal movement of an expander element within said post.

11. A prosthetic tibial component according to claim 5 wherein said mount comprises the groove, and further wherein said bearing construct comprises the tongue for seating in said groove.

12. A prosthetic tibial component according to claim 1 wherein said base construct comprises metal and said bearing construct comprises polyethylene.

13. A prosthetic component for a joint, said prosthetic component comprising:
 a base construct for engaging a first bone of the joint, the base construct comprising a bore;
 a bearing construct for engaging a second bone of the joint, the bearing construct comprising one of a horizontally-oriented tongue and groove; and
 a mount interposed between the base construct and the bearing construct for mounting the bearing construct to the base construct, the mount comprising (i) a post configured for positioning within the bore of the base construct and rotation to a user-selected angular orientation after the base construct has been disposed in a bone, and (ii) a locking mechanism for locking the post within the bore of the base construct with the user-selected angular orientation after the base construct has been disposed in a bone, so as to secure the mount to the base construct with the user-selected angular orientation, and the mount further comprising the other of the horizontally-oriented tongue and groove for slidably receiving the bearing construct and locking the bearing construct to the mount;
 wherein the horizontally-oriented groove comprises two vertically-extending walls, with each vertically-extending wall terminating in a horizontally-extending projection, and with the two vertically-extending walls being spaced from one another;
 wherein the horizontally-oriented tongue comprises a vertically-extending member terminating in a pair of laterally-extending projections;
 and further wherein the vertically-extending member of the tongue is sized to fit between the horizontally-extending projections of the groove and the pair of laterally-extending projections of the tongue are sized to fit between the pair of vertically-extending walls of the groove.

14. A prosthetic component according to claim 13 wherein said mount is angularly adjustably fixedly mountable to said baseplate.

\* \* \* \* \*